United States Patent
Legay et al.

(12) 
(10) Patent No.: US 11,857,238 B2
(45) Date of Patent: Jan. 2, 2024

(54) RATCHET SYSTEM FOR SCREWDRIVERS AND ITS USE

(71) Applicant: INNOPROD MEDICAL, Plaisance du Touch (FR)

(72) Inventors: Philippe Alain Lucien Fernand Legay, Yville-sur-Seine (FR); Frédéric Peyre, Lasserre (FR)

(73) Assignee: INNOPROD MEDICAL, Plaisance du Touch (FR)

( * ) Notice: Subject to any disclaimer, the term of this patent is extended or adjusted under 35 U.S.C. 154(b) by 31 days.

(21) Appl. No.: 17/126,442

(22) Filed: Dec. 18, 2020

(65) Prior Publication Data
US 2021/0186583 A1 Jun. 24, 2021

(30) Foreign Application Priority Data
Dec. 20, 2019 (FR) ...................................... 1915269

(51) Int. Cl.
| | |
|---|---|
| A61B 17/88 | (2006.01) |
| B25B 13/46 | (2006.01) |
| B25B 15/04 | (2006.01) |
| B25B 23/00 | (2006.01) |
| A61B 17/00 | (2006.01) |

(52) U.S. Cl.
CPC ........ *A61B 17/8875* (2013.01); *B25B 13/463* (2013.01); *B25B 15/04* (2013.01); *B25B 23/0042* (2013.01); *A61B 2017/00407* (2013.01)

(58) Field of Classification Search
CPC ... B25B 13/463; B25B 15/04; B25B 23/0042; B25B 23/142; B25B 23/1427; A61B 17/8875; A61B 2017/00407
USPC .......................................... 81/60; 464/30–41
See application file for complete search history.

(56) References Cited

U.S. PATENT DOCUMENTS

| | | | | |
|---|---|---|---|---|
| 1,106,545 | A | | 8/1914 | Camus |
| 1,273,379 | A | * | 7/1918 | Knudson ............. B25B 23/0042 81/177.1 |
| 1,345,708 | A | * | 7/1920 | Schneider ............. B25B 23/106 81/439 |
| 1,431,901 | A | * | 10/1922 | Troutman ............... B25B 15/04 81/29 |
| 1,540,749 | A | * | 6/1925 | Beach ..................... B25B 17/00 81/34 |
| 1,704,067 | A | * | 3/1929 | Wick ..................... B25B 15/04 81/DIG. 2 |
| 1,708,766 | A | * | 4/1929 | Lochner .................. B25B 23/10 408/239 R |

(Continued)

FOREIGN PATENT DOCUMENTS

| | | |
|---|---|---|
| WO | 2004/096069 A1 | 11/2004 |
| WO | 2012/015660 A2 | 2/2012 |

*Primary Examiner* — Don M Anderson
*Assistant Examiner* — Jonathan R Zaworski
(74) *Attorney, Agent, or Firm* — Maier & Maier, PLLC (57) ABSTRACT

A click system. Also, a screwdriver that includes a ratchet system. The ratchet system includes at least one handle, at least one rod with a male distal end and a proximal end, an element of cooperation that includes at least two lugs and at least two grooves, each of the at least two grooves include a helical portion. The at least two lugs each cooperate in a predetermined rotation direction with one of the at least two grooves so as to allow the driving of the rod. The ratchet system may be used in mechanics, carpentry or surgery.

9 Claims, 7 Drawing Sheets

(56) References Cited

U.S. PATENT DOCUMENTS

| | | | | |
|---|---|---|---|---|
| 1,731,979 | A * | 10/1929 | Krummel | B25B 15/06 279/97 |
| 2,450,504 | A * | 10/1948 | Farson | B25B 15/04 81/436 |
| 2,507,167 | A * | 5/1950 | Lemmerman | B25B 15/06 81/436 |
| 2,543,441 | A * | 2/1951 | Crummey | B25B 19/00 81/463 |
| 2,797,564 | A * | 7/1957 | Bonneau | B25B 23/1427 81/475 |
| 3,035,451 | A * | 5/1962 | O'Connell | B25B 13/467 81/34 |
| 3,302,672 | A * | 2/1967 | Walton | B25B 15/004 81/461 |
| 3,958,469 | A * | 5/1976 | Meese | B25B 13/466 81/58.3 |
| 4,026,338 | A * | 5/1977 | Goebel | B25B 15/007 81/441 |
| 4,429,599 | A * | 2/1984 | La Sante, Sr. | B25B 15/004 411/404 |
| 4,561,507 | A * | 12/1985 | Liou | B25B 15/06 173/93 |
| 4,572,038 | A * | 2/1986 | Graham | B25F 5/029 81/439 |
| 5,030,043 | A * | 7/1991 | Fischer | B25D 17/005 81/436 |
| 5,056,386 | A * | 10/1991 | Chaconas | B25B 23/101 81/452 |
| 5,595,095 | A | 1/1997 | Hillinger | |
| 5,746,298 | A * | 5/1998 | Krivec | B25B 23/1427 464/41 |
| 5,819,611 | A * | 10/1998 | Kozak | B25B 13/485 81/441 |
| 5,875,694 | A * | 3/1999 | Graf | B25B 13/50 81/461 |
| 6,009,779 | A * | 1/2000 | Mastroni | B25B 23/0021 81/177.85 |
| 6,047,620 | A * | 4/2000 | Kozak | B25B 13/485 81/53.2 |
| 6,085,619 | A * | 7/2000 | Blake | B25B 23/0035 81/177.85 |
| 6,732,613 | B2 * | 5/2004 | Hsieh | B25B 15/02 81/58.3 |
| 7,243,580 | B2 * | 7/2007 | Frazee | A61B 17/8875 81/439 |
| 7,762,164 | B2 * | 7/2010 | Nino | B25B 23/1427 81/475 |
| 7,938,046 | B2 * | 5/2011 | Nino | B25B 15/02 81/475 |
| 7,947,047 | B2 * | 5/2011 | Arnal | A61B 17/8875 606/104 |
| 8,028,608 | B2 * | 10/2011 | Sixto, Jr. | A61B 17/888 81/436 |
| 8,365,641 | B2 * | 2/2013 | Daglow | B25B 23/1427 81/476 |
| 8,439,593 | B2 * | 5/2013 | Slater | A61F 2/4684 403/348 |
| 9,241,751 | B2 * | 1/2016 | Nino | B25B 23/141 |
| 9,451,954 | B2 * | 9/2016 | Moore | A61B 17/0642 |
| 9,757,845 | B2 * | 9/2017 | Nassab | B25B 15/02 |
| 9,931,741 | B2 * | 4/2018 | Nino | A61B 17/8875 |
| 10,160,105 | B2 * | 12/2018 | Nino | B25B 23/1427 |
| 10,660,687 | B2 * | 5/2020 | Goodwin, Jr. | B25B 23/142 |

* cited by examiner

RATCHET SYSTEM FOR SCREWDRIVERS AND ITS USE

FIELD

The present invention relates to the field of tools. In particular, the present invention relates to a ratchet system applicable to a tool for screwing or unscrewing.

BACKGROUND

To be effective when screwing or unscrewing different parts of an assembly, it is necessary to be able to screw without the risk of unscrewing inadvertently. This is particularly true in the field of orthopedic surgery where it is essential to be able to be precise and efficient when screwing or unscrewing orthopedic elements.

It is known to those skilled in the art to use ratchet screwdrivers which make it possible to block the direction of rotation depending on whether the user seeks to screw or unscrew. EP 1617773 describes a ratchet screwdriver used in surgery comprising a handle, a drive mechanism, a ratchet mechanism and a locking mechanism. The ratchet mechanism is interposed between the handle and the drive mechanism, a locking mechanism holds the handle on the ratchet mechanism. However, this type of system involves systematically and completely disassembling the screwdriver in order to clean and sterilize it, a mandatory step for all medical use. Systematic and repeated dismantling of the ratchet mechanism makes the screwdriver fragile, causing it to lose its seal, thus creating risks of contamination. This type of screwdriver is also very expensive.

There is therefore a real demand for surgical screwdrivers making it possible to block a direction of rotation while being easily sterilizable and cleanable.

The object of the present invention is therefore to provide a snap-fastening system suitable for use in a surgical screwdriver making it possible to cause a rotation in the desired direction, and to prevent any contrary unwanted movement, by a simple mechanical principle and easily cleanable and sterilizable without risk of premature deterioration. This ratchet system does not include a complex mechanism to disassemble during sterilization, making it robust and easy to use.

SUMMARY

The present invention relates to a ratchet system comprising:
- at least one handle comprising a distal end and a connection surface;
- at least one rod comprising a male distal end, a proximal end and a contact surface, said proximal end comprising a cavity;
- cooperation means including:
  - at least two lugs positioned on the distal end of the handle;
  - at least two grooves positioned on the internal wall of the cavity of the rod, each of the at least two grooves comprising a helical portion, one of the ends of which is a wall perpendicular to said internal wall;
- the at least two lugs each cooperating in a predetermined rotation direction with one of the at least two grooves so as to be in contact with said perpendicular wall said contact allowing the driving, in said predetermined rotation direction, of the rod by the handle;

wherein the proximal end of the rod is adapted to cooperate with the distal end of the handle through the cooperating means until contact between the connection surface with the contact surface in order to drive the rod in the same rotation direction.

In one embodiment, the at least one rod is a screw rod. In one embodiment, the at least one rod is an unscrewing rod. In one embodiment, the proximal end of the at least one rod and the distal end of the at least one handle are cylindrical in shape.

The invention further to a ratchet system comprising:
- at least one handle comprising a distal end, said distal end comprising a cavity;
- at least one rod comprising a male distal end and a proximal end;
- means of cooperation including:
  - at least two grooves positioned on the internal wall of the cavity of the handle, each of the at least two grooves comprising a helical portion, one of the ends of which is a wall perpendicular to said internal wall;
  - at least two lugs positioned on the proximal end of the rod;
- the at least two lugs each cooperating in a predetermined rotation direction with one of the at least two grooves until coming into contact with said perpendicular wall, said contact allowing the driving, in the predetermined rotation direction, of the rod, by the handle;

wherein the proximal end of the rod is adapted to cooperate with the distal end of the handle through the cooperation means in order to drive the rod in the same rotation direction.

In one embodiment, the at least one handle is a screwing handle. In one embodiment, the at least one handle is an unscrewing handle. In one embodiment, the proximal end of the at least one rod and the distal end of the at least one handle are cylindrical in shape. The invention also relates to a screwdriver comprising a ratchet system according to the invention.

In the present invention, the terms below are defined as follows:
- "downward" relates to an orientation going from the proximal end to the distal end of an object.
- "unscrewing" relates to an anti-clockwise direction of rotation.
- "perpendicular wall" relates to a first wall describing an angle of approximately 90° with a second wall.
- "groove" concerns a path carved into a wall. The terms groove, path, channel, notch, gutter, groove, slot, groove or slide can be used interchangeably.
- "screwing" relates to a clockwise direction of rotation.

BRIEF DESCRIPTION OF THE DRAWINGS

The following description will be better understood on reading the drawings. For the purpose of illustration, the device is shown in preferred embodiments. It should be understood, however, that the present application is not limited to the precise arrangements, structures, features, embodiments and appearance indicated on those drawings. The drawings are not drawn to scale and are not intended to limit the scope of the claims to the embodiments shown in these drawings. Therefore, it should be understood that when features mentioned in the claims are followed by references, said references are included only for the purpose of improving the understanding of the claims and in no way limit the scope of those claims.

DETAILED DESCRIPTION

The present invention relates to a ratchet system.

The ratchet system comprises:
- at least one handle comprising a distal end and a connection surface;
- at least one rod comprising a male distal end, a proximal end and a contact surface, said proximal end comprising a cavity;
- cooperation means including:
  - at least two lugs positioned on the distal end of the handle;
  - at least two grooves positioned on the internal wall of the cavity of the rod, each of the at least two grooves comprising a helical portion, one of the ends of which is a wall perpendicular to said internal wall;

the at least two lugs each cooperating in a predetermined rotation direction with one of the at least two grooves so as to be in contact with said perpendicular wall, said contact allowing the driving, in the predetermined rotation direction, of the rod, by the handle; wherein the proximal end of the rod is adapted to cooperate with the distal end of the handle through the cooperating means until contact between the connection surface with the contact surface, in order to drive the rod in the same rotation direction.

The distal end of the handle is configured to fit into the cavity formed in the proximal end of the rod. During this operation, the lugs are supported and slide along the grooves dug in said cavity until they are each in contact with a perpendicular wall machined in the internal wall of the cavity, and that the connection surface of the handle is in contact with the contact surface of the rod. The walls perpendicular to the internal wall of the cavity of the proximal part of the rod are then rotated by the lugs in a predefined direction of rotation by the downward orientation (from the proximal end to the distal end) of the grooves: clockwise or anti-clockwise. As a result, a rotational movement is applied to the rod.

If, by an untimely gesture, the handle is actuated in a direction of rotation opposite to that predefined by the downward orientation of the grooves, the lugs separate from the perpendicular walls, their ends slide and go up on the grooves, thus preventing training of the rod rotating in the direction of rotation opposite to the predefined one.

The ratchet system of the invention therefore advantageously makes it possible to control a direction of rotation, clockwise or anti-clockwise, to transmit a movement in a determined direction and, above all, to prevent any untimely gesture from leading to the transmission of the movement. reverse. This is particularly useful for use of said system in a screwdriver since only one direction of rotation, corresponding to screwing or unscrewing, can be applied to the rod.

In the case of a screwdriver comprising the ratcheting system according to the invention, said system makes it possible to screw without the risk of inadvertently unscrewing and, conversely, of unscrewing without the risk of inadvertently screwing any object composed of one or more elements.

The handle is configured in a way that the lugs separate from the wall when the handle is moved in the opposite direction than the predetermined direction.

The rod is a drive mechanism, able to drive a screw for example in a chosen direction of rotation.

According to one embodiment, the at least one rod is a screw rod.

According to one embodiment, the at least one rod is an unscrewing rod.

According to one embodiment, the ratchet system comprises a screwing rod and an unscrewing rod.

According to one embodiment, the proximal end of the at least one rod and the distal end of the at least one handle displays a cylindrical shape.

According to one embodiment, the ratchet system is dismountable. In this embodiment, the elements of said ratchet system (handle, rod) are independent of each other and can be separated, advantageously for easy cleaning.

According to one embodiment, the ratchet system is sterilizable.

According to one embodiment, the various elements of the ratchet system can be sterilized.

According to one embodiment, the ratchet system further comprises a handle. In this embodiment, the handle is connected to the handle by a connection surface.

According to one embodiment, the handle comprises a shaft. In this embodiment, the handle and the shaft can be merged, i.e., be the same element of the ratchet system.

According to one embodiment, the distal end of the handle displays a cylindrical shape. This embodiment is particularly advantageous because the cylindrical shape facilitates the rotation of the distal end of the handle. Another shape could indeed hinder the rotation of the distal end of the handle.

According to one embodiment, the ratchet system includes the same number of lugs and grooves.

According to one embodiment, the ratchet system comprises at least 2, 3, 4, 5, 6, 7, 8, 9, or 10 lugs distributed over the distal end of the handle. The number of lugs determines the rotation of the wrist to screw or unscrew comfortably while being effective. The presence of 3 lugs is particularly advantageous in terms of efficiency, especially in the case of screwing. The presence of 6 pins is particularly advantageous in terms of precision.

According to one embodiment, the ratchet system comprises 2 lugs distributed over the distal end of the handle.

According to one embodiment, the ratchet system comprises 2 lugs distributed over the distal end of the handle and 2 grooves positioned on the internal wall of the cavity of the rod.

According to one embodiment, the ratchet system comprises 3 lugs distributed over the distal end of the handle. The presence of 3 lugs is particularly advantageous in terms of efficiency, especially in the case of screwing. The presence of 3 lugs equally distributed around the distal end of the handle offers a more comfortable and a more physiologically adapted handling.

According to one embodiment, the ratchet system comprises 3 lugs distributed over the distal end of the handle and 3 grooves positioned on the internal wall of the cavity of the rod.

According to one embodiment, the at least two lugs are evenly distributed over the distal end of the handle.

According to one embodiment, the at least two lugs have rounded ends. This embodiment is particularly advantageous because the rounded shape of the ends of the lugs allows the reversible movement consisting in being engaged and disengaged in the at least two grooves positioned on the internal wall of the cavity of the rod.

According to one embodiment, the at least one rod comprises a cylindrical body. This embodiment is particularly advantageous because the cylindrical shape makes it possible to limit the friction between the rod and another element of the screwing system.

According to one embodiment, at least one rod has a length of between 1 and 50 cm, preferably between 5 and 40 cm, more preferably between 5 and 20 cm.

According to one embodiment, the length of the at least one rod depends on the use made of the screwing system. For example, for applications in interventional radiology in particular, or in surgery in general, a short rod (that is to say having a length between 5 and 10 cm) will be used for screwing/unscrewing specific screws in small superficial bones such as vertebrae; a long rod (i.e. having a length greater than 20 cm) will be used for bones such as those of the pelvis (pelvis and sacrum).

According to one embodiment, the proximal end of the at least one rod is cylindrical in shape.

According to one embodiment, the proximal end of the at least one rod has a length of between 1 and 10 cm, preferably between 1 and 5 cm.

According to one embodiment, the length of the proximal end of the at least one rod depends on the use made of the screwing system. For example, for applications in interventional radiology in particular, or in surgery in general, a short rod (that is to say having a length between 5 and 10 cm) will be used for screwing/unscrewing specific screws in small superficial bones such as vertebrae; a long rod (i.e. having a length greater than 20 cm) will be used for bones such as those of the pelvis (pelvis and sacrum).

According to one embodiment, the proximal end of the at least one rod has a diameter of between 0.1 and 5 cm, preferably between 0.2 and 2 cm.

According to one embodiment, the diameter of the proximal end of the at least one rod depends on the use made of the screwing system. In particular, a short stem (length between 5-10 cm) will have a smaller diameter than a long stem (length greater than 20 cm).

According to one embodiment, the proximal end of the at least one rod is a bore.

According to one embodiment, the proximal end of the at least one rod is a bore comprising at least two threads.

According to one embodiment, the at least two grooves are also distributed over the inner wall of the proximal end of the at least one rod.

According to one embodiment, the at least two grooves are machined in the inner wall of the proximal end of the at least one rod.

According to one embodiment, the at least two grooves are obtained by turning the internal wall of the proximal end of the at least one rod.

According to one embodiment, the at least two grooves each describe a channel of helical or sinusoidal shape on the inner wall of the proximal end of the at least one rod.

According to one embodiment, the at least two grooves extend between the proximal end and the distal end of the at least one rod over a distance of between 0.5 and 5 cm, preferably between 0.5 and 3 cm.

According to one embodiment, the distance at which the at least two grooves extend between the proximal end and the distal end of the at least one rod depends on the use made of the screwing system.

According to one embodiment, the at least two grooves each comprise a helical portion descending from the proximal end of the rod towards the distal end of the rod.

According to one embodiment, the at least two grooves each comprise a helical portion descending from the proximal end of the rod towards the distal end of the rod in a clockwise direction.

According to one embodiment, the at least two grooves each comprise a helical portion descending from the proximal end of the rod towards the distal end of the rod in a counterclockwise direction.

According to one embodiment, the at least two grooves each describe a downward slope in a clockwise direction from the proximal end of the at least one rod towards the distal end of the at least one rod.

According to one embodiment, the at least two grooves each describe a downward slope in a counterclockwise direction from the proximal end of the at least one rod towards the distal end of the at least one rod.

According to one embodiment, the depth of the at least two grooves depends on the diameter of the rod and on the number of grooves.

According to one embodiment, the at least two grooves each have a length of between 0.5 and 5 cm, preferably between 0.5 and 3 cm.

According to one embodiment, the length of the at least two grooves depends on the use made of the screwing system.

According to one embodiment, the at least two grooves each have a helical radius of between 0.1 and 5 cm, preferably between 0.2 and 2 cm.

According to one embodiment, the helical radius of the at least two grooves depends on the use made of the screwing system, more precisely, it depends on the diameter of the rod.

According to one embodiment, the at least two grooves are internal threads.

According to one embodiment, the walls perpendicular to the internal wall of the cavity are machined in the internal wall of the proximal end of the at least one rod.

According to one embodiment, the proximal end of the at least one rod and the distal end of the at least one handle are cylindrical in shape.

According to one embodiment, the ratchet system is a screwing and/or unscrewing means.

According to one embodiment, the latching system is a screwdriver, a key, or any other screwing and/or unscrewing means known to those skilled in the art.

According to one embodiment, the ratchet system is a screwdriver suitable for use in surgery.

According to one embodiment, the ratchet system is a screwdriver suitable for use in orthopedic surgery.

According to one embodiment, the ratchet system is a surgical tool.

According to one embodiment, the ratchet system is a surgical screwdriver.

According to one embodiment, the latching system is suitable for screwing and/or unscrewing an object comprising one or more elements. In this embodiment, the elements are assembled or pre-assembled by threaded or tapped joints, with conventional or reverse pitches.

The present invention also relates to a ratchet system.

The invention relates to a ratchet system comprising:
- at least one handle comprising a distal end, said distal end comprising a cavity;
- at least one rod comprising a male distal end and a proximal end;
- means of cooperation including:
  - at least two grooves positioned on the internal wall of the cavity of the handle, each of the at least two grooves comprising a helical portion, one of the ends of which is a wall perpendicular to said internal wall;
  - at least two lugs positioned on the proximal end of the rod;
  - the at least two lugs each cooperating with one of the at least two grooves until coming into contact with said perpendicular wall;
- wherein the proximal end of the rod is adapted to cooperate with the distal end of the handle through the cooperation means.

In one embodiment, the at least one handle is a screw handle.

In one embodiment, the at least one handle is an unscrewing handle.

In one embodiment, the ratchet system includes a screwing handle and an unscrewing handle.

In one embodiment, the proximal end of the at least one rod and the distal end of the at least one handle are cylindrical in shape.

The handle and its distal end, the rod and its proximal end, the cooperation means, namely the lugs, grooves and perpendicular walls are as described above.

The present invention is about a ratchet system.

The ratchet system includes:
- at least one handle comprising a distal end and a connection surface;
- at least one rod comprising a male distal end, a proximal end and a contact surface;
- means of cooperation including:
  - at least two lugs;
  - at least two grooves positioned on the internal wall of a cavity, each of the at least two grooves comprising a helical portion, one end of which is a wall perpendicular to said internal wall;
  - the at least two lugs each cooperating with one of the at least two grooves until they come into contact with said perpendicular wall;
- wherein the proximal end of the rod is adapted to cooperate with the distal end of the handle through the cooperating means until contact between the connection surface with the contact surface.

In one embodiment, the at least two lugs are positioned on the distal end of the handle.

In one embodiment, the proximal end of the rod comprises a cavity, and the at least two grooves positioned on the inner wall of the cavity of the rod, each of the at least two grooves comprising a helical portion of which one end is a wall perpendicular to said internal wall.

In one embodiment, the at least two lugs are positioned on the proximal end of the rod.

In one embodiment, the distal end of the handle comprises a cavity, and the at least two grooves positioned on the internal wall of the handle cavity, each of the at least two grooves comprising a helical portion of which one end is a wall perpendicular to said internal wall.

The invention also relates to a screwdriver comprising a ratchet system according to the present invention.

In one embodiment, the screwdriver is a surgical screwdriver, or suitable for use in surgery, preferably in orthopedic surgery.

The invention also relates to the use of the ratchet system in a device requiring control of a direction of rotation of a rod.

The invention also relates to the use of the ratchet system in a screwing and/or unscrewing means.

The invention also relates to the use of the ratchet system in a screwdriver, a key, or any other screwing and/or unscrewing means known to those skilled in the art.

The invention also relates to the use of the ratchet system in a screwdriver suitable for use in surgery.

The invention also relates to the use of the ratchet system in a screwdriver suitable for use in orthopedic surgery.

The invention also relates to the use of the ratchet system in a screwdriver suitable for use in interventional radiology.

The invention also relates to the use of the ratchet system in a surgical tool, a surgical screwdriver.

The invention also relates to the use of the ratchet system in mechanics, carpentry or surgery. Although various embodiments have been described and illustrated, the detailed description should not be construed as being limited thereto. Various modifications can be made to the embodiments by those skilled in the art without departing from the true spirit and scope of the disclosure as defined by the claims.

Embodiments Illustrating the Invention

Figure 1:
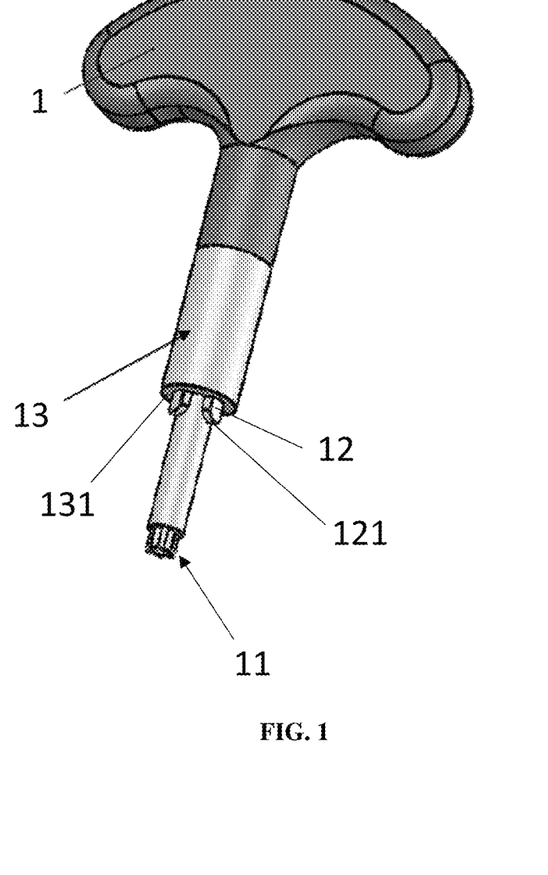
FIG. 1 is a general perspective view of the handle according to a first embodiment of the invention.
Figure 2A:
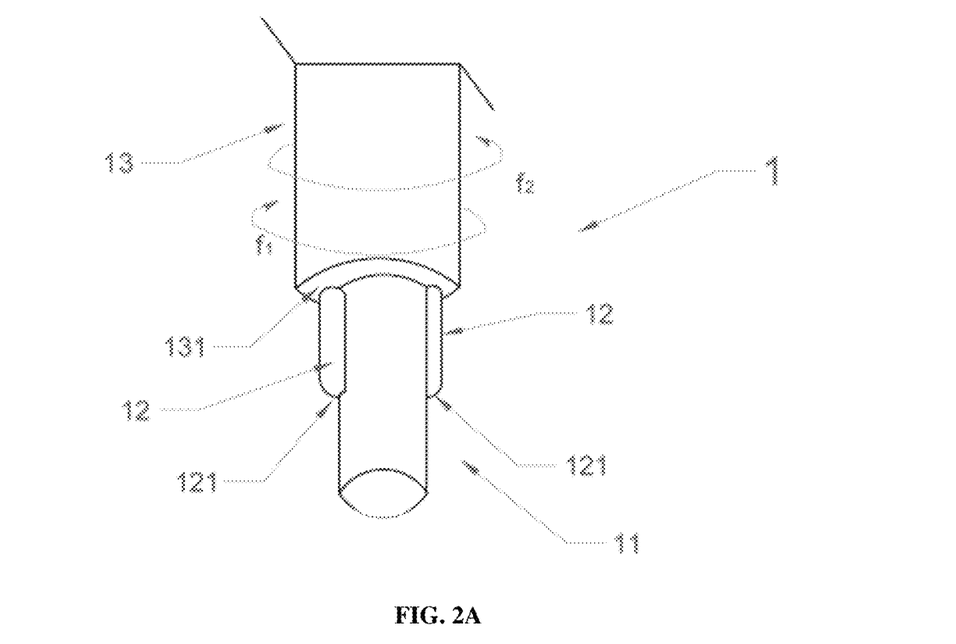
FIG. 2A is a three-dimensional view of distal end of the handle according to a first embodiment of the invention.
Figure 2B:
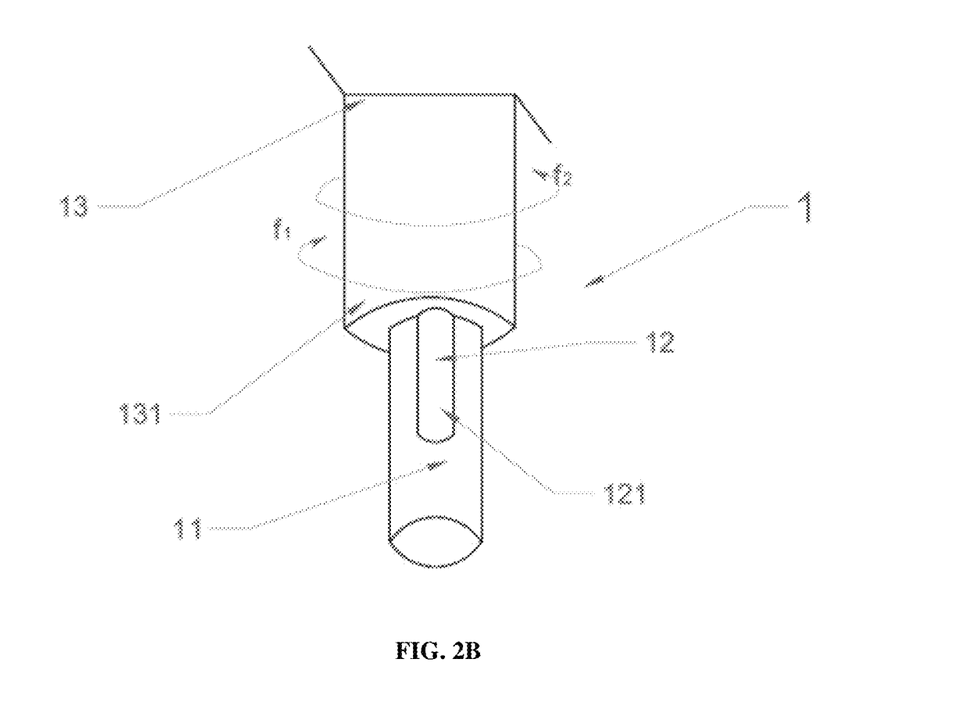
FIG. 2B is a three-dimensional view of the distal end handle according to a first embodiment of the invention.

As illustrated in FIGS. 1, 2A and 2B, the handle 1 includes:
- a handle 13;
- a cylindrical distal end 11 linked to the handle 13 by a connection surface 131 extending preferably perpendicular to the axis of revolution of the cylindrical distal end 11;
- two lugs 12 equally distributed around said distal end 11, having rounded ends 121. In the embodiments of FIGS. 2A and 2B said lugs 12 are two, and they are diametrically opposed. The lugs 12 extend parallel to the axis of revolution of the cylindrical distal end 11.

Figure 3A:
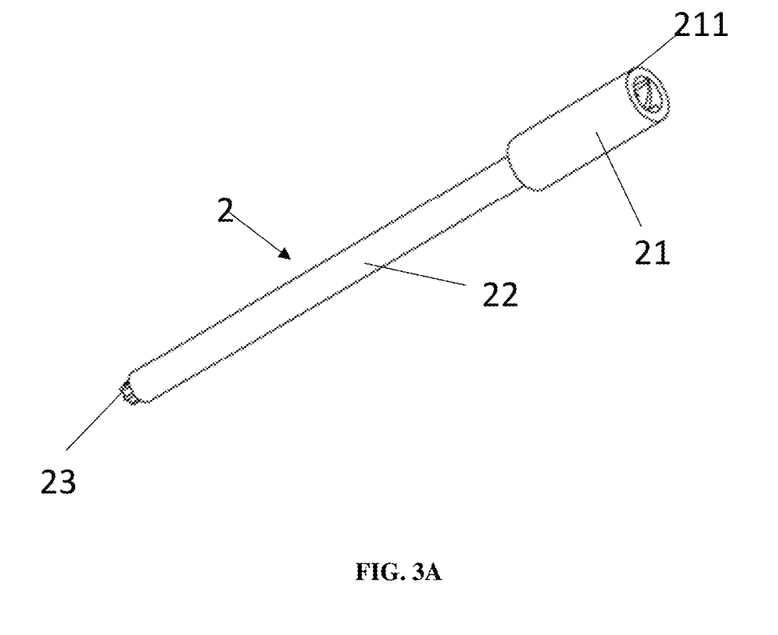
FIG. 3A is a three-dimensional perspective view of a screw rod according to one embodiment of the invention.
Figure 4A:
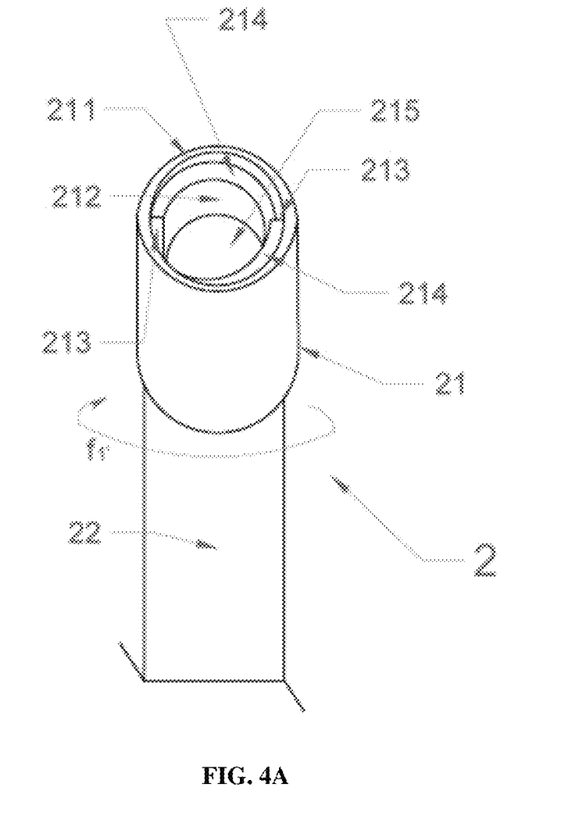
FIG. 4A is a three-dimensional view of a proximal end of a screw rod according to one embodiment of the invention.
Figure 4B:
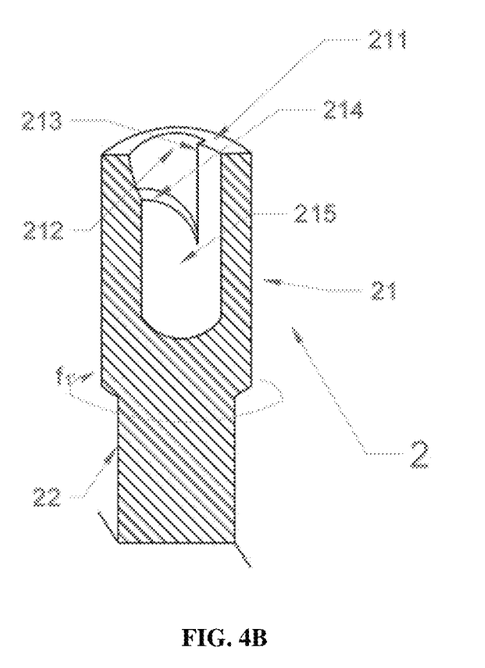
FIG. 4B is a sectional view of a proximal end of a screw rod according to one embodiment of the invention.

As illustrated in FIGS. 3A, 4A and 4B, the screw rod 2 comprises a cylindrical rod 22 comprising a male distal end 23 and a cylindrical proximal end 21. The proximal end 21 comprises a cavity 215 displaying internal walls 212. Two grooves 214 are machined in the internal wall 212 of the cavity 215, the two grooves 214 comprising a helical portion descending from the proximal end of the rod 21 towards the distal end 23 of the rod 2 in a clockwise direction. The cavity 212 further comprises two walls 213 perpendicular to the internal wall 212 of the cavity 215. The screw rod 2 displays a contact surface aimed at cooperating with the connection surface 131 of the handle 13.

The distal end 11 of the handle 13 is configured to fit into the cavity 215 formed in the proximal end 21 of the screwing rod 2. During this operation, the two lugs 12 are supported and slide along the two grooves. 214 carved into said cavity 215 until said lugs 12 are each in abutment contact with one perpendicular wall 213 machined in the internal wall 212 of the cavity 215 of the proximal end 21 of the rod 2, and the connection surface 131 is in contact with the opposite contact surface 211 of the screw rod 2. The walls 213 perpendicular to the internal wall 212 of the cavity 215 of the proximal part of the rod 21 are then rotated by said lugs 12 in the clockwise rotation direction f1, f1'. It follows that a rotational movement, and more particularly, a screwing movement, is applied to the screwing rod 2.

In this embodiment, when the shaft 13, of the handle 1 is coupled with the screwing rod 2 and is actuated in the clockwise direction f1, meaning screwing, the lugs 12 of said handle 1 come to cooperate with the perpendicular walls 213, so that the surface of the connection surface 131 is in abutment contact with the contact surface 211, so as to drive the rod 2 in the same clockwise direction f1', meaning screwing it.

This embodiment is particularly advantageous because if, by an untimely gesture, said handle 1 is actuated in the counterclockwise direction f2, meaning unscrewing, the lugs 12 separate from the walls 213, their ends 121 slide and go up on the grooves 214, thus preventing the driving of the screw rod 2.

This embodiment is also advantageous because the distal end 11 of the handle 1 remains trapped in the cavity 215, so that said handle 1 is not separated from the screw rod 2, to allow it to be actuated again clockwise f1, meaning screwing, to drive the screwing rod 2 in the clockwise direction f1', meaning screwing.

Figure 3B:
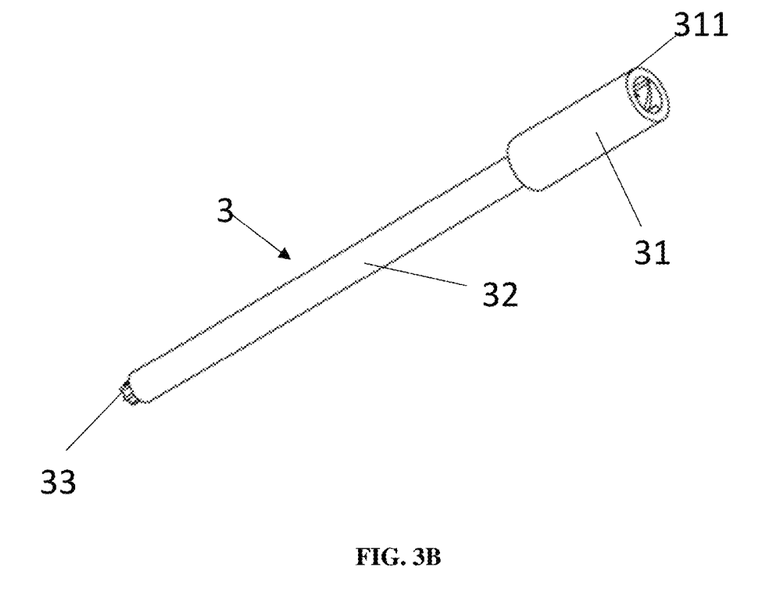
FIG. 3B is a three-dimensional perspective view of an unscrew rod according to one embodiment of the invention.
Figure 5:
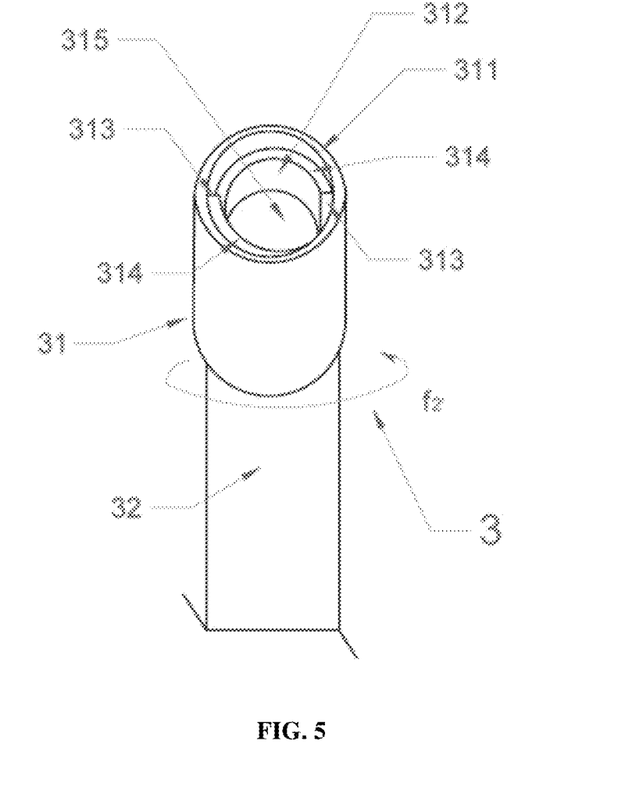
FIG. 5 is a three-dimensional view of an unscrewing rod according to one embodiment of the invention.
Figure 6:
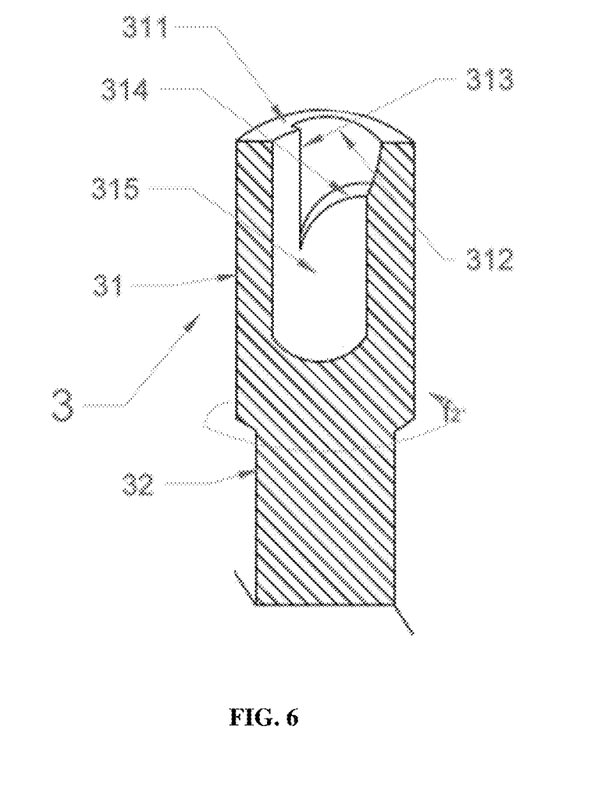
FIG. 6 is a sectional view of an unscrewing rod according to one embodiment of the invention.

As illustrated in FIGS. 3B, 5 and 6, the unscrewing rod 3 comprises, similarly to the screwing rod 2:
a cylindrical rod 32 comprising a male distal end 33 and a cylindrical proximal end 31, said proximal end 31 comprising a cavity 315;
two grooves 314 machined in the internal walls 312 of the cavity 315, the two grooves 314 comprising a helical portion descending from the proximal end 31 of the unscrewing rod 3 towards the distal end 33 of the unscrewing rod 3 in a counterclockwise direction; and
two walls 313 perpendicular to the internal wall 312 of the cavity 315.

In a similar way to the screwing rod 2, the distal end 11 of the handle 13 is configured to fit into a cavity 315 formed in the proximal end 31 of the unscrewing rod 3. During this operation, the two lugs 12 are supported and slide along two grooves. 314 carved out in said cavity 315 until said lugs 12 are each in contact with a perpendicular wall 313 machined in the internal wall 312 of the cavity 315 of the proximal part of the rod, and the surface of the connection surface 131 is in contact with a contact surface 311 of the rod 3. The walls 313 perpendicular to the internal wall 312 of the cavity 315 of the proximal part 31 of the unscrewing rod 3 are then rotated by said lugs 12 in the direction of anti-clockwise rotation f2, f2'. As a result, a rotational movement, and more particularly, an unscrewing movement, is applied to the unscrewing rod 3.

In this embodiment, when the shaft 13, of the handle 1 is coupled with the unscrewing rod 3 and is actuated in the counterclockwise direction of the arrow f2, meaning unscrewing, the lugs 12 of said handle 1 cooperate with the walls 313, until the surface of the connection surface 131 is in contact with the contact surface 311, so as to drive the unscrewing rod 3 in the same counterclockwise direction f2', meaning unscrewing.

This embodiment is particularly advantageous because if, by an inadvertent gesture, said handle 1 is actuated in the clockwise direction f1, meaning screwing, the lugs 12 separate from the walls 313, their ends 121 slide and go up on the grooves 314, thus preventing the driving of the unscrewing rod 3.

This embodiment is also advantageous because the distal end 11 of the handle 1 remains trapped in the cavity 315, so that said handle 1 is not separated from the unscrewing rod 3, to allow it to be actuated by again in the counterclockwise direction f2, meaning unscrewing, to drive the unscrewing rod 3 in the counterclockwise direction f2', meaning unscrewing.

The invention claimed is:

1. A screwdriver comprising a ratchet system configured to connect a handle to a rod, the ratchet system comprising:
at least one handle comprising a cylindrical distal end extending along a first axis of revolution and further comprising a connection surface extending perpendicular to the first axis of revolution of the cylindrical distal end;
at least one rod comprising a male distal end, a cylindrical proximal end extending along a second axis of revolution and a contact surface, said cylindrical proximal end comprising a cavity presenting an internal wall; and
cooperation means including:
at least two lugs positioned on the distal end of the at least one handle; and
at least two grooves positioned on the internal wall of the cavity and extending from the contact surface towards the proximal end of the at least one rod, each of the at least two grooves comprising a helical portion, one end of which is a flat perpendicular wall to said inner wall;
the at least two lugs each cooperating in only a predetermined rotation direction with one of the at least two grooves so as to be in contact with said flat perpendicular wall, said contact allowing driving, in the predetermined rotation direction, of the at least one rod by the at least one handle;
wherein the cylindrical proximal end of the at least one rod can cooperate with the distal end of the at least one handle by means of the cooperation means until abutment contact between the connection surface with the contact surface is established in order to align the first and second axis of revolution and drive the at least one rod in the same rotation direction; and
wherein the at least one handle is configured in a way that the at least two lugs separate from said flat perpendicular wall when the at least one handle is rotated in a rotation direction opposite the predetermined rotation direction so that the at least one rod is prevented from driving in the opposite rotation direction, and the at least one handle remains trapped in the cavity, in order to allow driving of the at least one rod in the predetermined rotational direction when the at least one handle is rotated in the predetermined rotation direction.

2. The screwdriver according to claim 1, wherein the predetermined rotation direction is a clock-wise rotation direction.

3. The screwdriver according to claim 1, wherein one of the at least one rod is a screw rod.

4. The screwdriver according to claim 1, wherein one of the at least one rod is an unscrewing rod.

5. A method of screwing or unscrewing screws in bones in orthopedic surgery, comprising screwing or unscrewing screws in bones with the screwdriver comprising the ratchet system according to claim 1, the screwdriver being suitable for use in orthopedic surgery.

6. A screwdriver comprising a ratchet system configured to connect a handle to rod, the ratchet system comprising:

at least one handle comprising a cylindrical distal end extending along a first axis of revolution, said cylindrical distal end comprising a cavity presenting an internal wall with a contact surface;

at least one rod comprising a male distal end extending along a second axis of revolution and a cylindrical proximal end with a connection surface; and cooperation means including:
  at least two grooves positioned on the internal wall of the cavity, each of the at least two grooves comprising a helical portion, one of the ends of which is a flat wall perpendicular to said internal wall and extending from the contact surface towards the proximal end of the at least one handle; and
  at least two lugs positioned on the proximal end of the at least one rod;
  the at least two lugs each cooperating in only a predetermined rotation direction with one of the at least two grooves until they come into contact with said flat perpendicular wall, said contact allowing the leading, in the predetermined rotation direction of the at least one rod by the at least one handle;

wherein the proximal end of the at least one rod is adapted to cooperate with the distal end of the at least one handle via the cooperating means until abutment contact between the connection surface with the contact surface is established in order to align the first and second axis of revolution, and to lead the at least one rod in a same rotation direction as the predetermined rotation direction of the at least one handle; and wherein the at least one rod is configured in a way that the at least two lugs separate from said flat perpendicular wall when the at least one handle is rotated in a rotation direction opposite the predetermined rotation direction so that the at least one rod is prevented from driving in the opposite rotation direction, and the at least one rod remains trapped in the cavity, in order to allow driving of the rod in the predetermined rotational direction when the handle is rotated in the predetermined rotation direction.

7. The screwdriver according to claim 6, wherein one of the at least one handle is a screw handle and the predetermined rotation direction is a clockwise rotation direction.

8. The screwdriver according to claim 6, wherein one of the at least one handle is an unscrewing handle and the predetermined rotation direction is a counter-clockwise rotation direction.

9. A method of screwing or unscrewing screws in bones in orthopedic surgery, comprising screwing or unscrewing screws in bones with the screwdriver comprising the ratchet system according to claim 6, the screwdriver being suitable for use in orthopedic surgery.

* * * * *